(12) United States Patent
Segura Ruiz et al.

(10) Patent No.: US 10,562,958 B2
(45) Date of Patent: Feb. 18, 2020

(54) METHOD FOR PRODUCING INJECTABLE FORMULATIONS OF BLOOD-DERIVED PROTEIN MATERIALS, AND MATERIALS OBTAINED USING SAID METHOD

(75) Inventors: Álvaro Segura Ruiz, San José (CR); Mariángela Vargas Arroyo, San José (CR); Guillermo León Montero, Alajuela (CR); Mauren Villalta Arrieta, San José (CR); María Herrera Vega, Cartago (CR); Yamileth Angulo Ugalde, San José (CR)

(73) Assignee: UNIVERSIDAD DE COSTA RICA, San Jose (CR)

( * ) Notice: Subject to any disclaimer, the term of this patent is extended or adjusted under 35 U.S.C. 154(b) by 0 days.

(21) Appl. No.: 14/110,594

(22) PCT Filed: Apr. 8, 2011

(86) PCT No.: PCT/CR2011/000001
§ 371 (c)(1),
(2), (4) Date: Dec. 26, 2013

(87) PCT Pub. No.: WO2012/136172
PCT Pub. Date: Oct. 11, 2012

(65) Prior Publication Data
US 2014/0121357 A1   May 1, 2014

(51) Int. Cl.
| C07K 14/765 | (2006.01) |
| C07K 16/06 | (2006.01) |
| C07K 16/18 | (2006.01) |
| C07K 1/16 | (2006.01) |
| C07K 1/36 | (2006.01) |
| C07K 1/34 | (2006.01) |
| A61L 2/00 | (2006.01) |

(52) U.S. Cl.
CPC .......... *C07K 14/765* (2013.01); *C07K 16/065* (2013.01); *C07K 16/18* (2013.01); *A61L 2/0017* (2013.01); *A61L 2/0023* (2013.01); *C07K 1/36* (2013.01)

(58) Field of Classification Search
None
See application file for complete search history.

(56) References Cited

U.S. PATENT DOCUMENTS 4,177,188 A * 12/1979 Hansen ............. C07K 14/765
530/364
4,886,779 A * 12/1989 Hilfenhaus ........... A61L 2/0088
435/236

OTHER PUBLICATIONS

Rosa, P.A.J., et al. 2007 Journal of Chromatography A 1141: 50-60.*
WHO. 2004 World Health Organization Technical Report, series No. 924, annex 4: 150-224.*
Page, M., et al. 1996 The Protein Protocols Handbook: 723.*
Dove, G.B., et al. 1986 "Recovery of Proteins from Polyethylene Glycol-Water Solution by Salt Partition" in Separation, Recovery, and Purification in Biotechnology: 93-108.*

* cited by examiner

*Primary Examiner* — Marsha Tsay
(74) *Attorney, Agent, or Firm* — Lucas & Mercanti, LLP

(57) ABSTRACT

A method for producing injectable pharmaceutical formulations of blood-derived protein materials includes the steps of fractioning the source material in a polymer/salt aqueous two-phase system in the presence of phenol, purifying the top phase of the system by means of precipitation with caprylic acid and purifying the bottom phase by means of thermocoagulation, increasing the purity of the materials in both phases through chromatography, removing viral particles by means of the nanofiltration of both preparations, and formulating, stabilizing, and packaging the resulting materials.

28 Claims, 6 Drawing Sheets

METHOD FOR PRODUCING INJECTABLE FORMULATIONS OF BLOOD-DERIVED PROTEIN MATERIALS, AND MATERIALS OBTAINED USING SAID METHOD

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN SUBMITTED ON COMPACT DISC

Not applicable.

BACKGROUND OF THE INVENTION

1. Field of the Invention

The present invention relates to the field of purification of therapeutic proteins, particularly to a method for the production of injectable formulations of blood-derived protein products such as immunoglobulin, and/or albumin.

2. Description of Related Art Including Information Disclosed Under 37 CFR 1.97 and 37 CFR 1.98

Products derived from blood plasma such as human albumin, human immunoglobulin and heterologous antivenoms are important drugs in the treatment of various diseases, accidents and injuries. Due to the present increased demand for these products, it is important to improve the efficiency of production methods thereof, to adequately supply this demand, and thus prevent a global shortage of these drugs in the short term.

To obtain protein products derived from blood, particularly plasma, there are several methods well known in the prior art. Among them we may find the following:

1. Plasma Fractionation

Cohn's technique for plasma fractionation (cold alcohol fractionating) is the most common method used by the plasma-derived biological products industry (see Cohn E J, Strong L E, Hughes W L, Mulford D J, Ashworth J N, Melin M. Taylor H L 1946. "Preparation and properties of serum and plasma proteins. IV. A system for the separation into fractions of the protein and lipoprotein components of biological tissue and fluids", Journal of the American Chemical Society, 68: 459-475). To improve those aspects related to the production cost and performance of the original technique, several researchers have proposed modifications employing less reactive or suppress steps in the process (see Wink J., Hidalgo J., Seeberg V., Johnson F E 1957. "Preparation and properties of a heat-treated human plasma protein fraction." Vox Sanguinis 2: 174-186; Kistler, P Nitschmann, H. 1962. "Large Scale Production of Human plasma Fractions", Vox Sanguinis 7: 414-424 Schneider, W., Wolter, D., McCarty, L. 1976, "Alternatives for Plasma Fractionation." Vox Sanguinis, (31) 2: 141-151). Moreover, other modifications suggest the incorporation of purification techniques based on the use of precipitating agents, one or more chromatographic steps or a combination thereof. Among the commonly used precipitating agents are ammonium sulfate, polyethylene glycol and caprylic acid.

2. Plasma Fractionation Using Aqueous Two-Phase Systems (ATPS).

It has been reported the use of aqueous two-phase systems (ATPS) for the primary recovery and fractionating of compounds of interest with high commercial value. The ATPS are composed of mixtures of polymer-polymer, polymer-salt or salt-alcohol, and have been used in the primary recovery and partial purification of biological products such as proteins, genetic material, cells or organdies thereof, organic compounds such as fragrances and dyes, heavy metals, and certain drugs (see Benavides, J., Rito-Palomares, M. 2008. "Review: Practical experiences from the development of two-phase Aqueous Processes for the recovery of high value biological products". J Chem Technol Biotechnol 3:133-142; Huddleston, J., A. Veide, K Kohler, J. Flanagan, S-0. Enfors and A. Lyddiat. 1991. "The molecular basis of partitioning in Aqueous two-phase systems". Tibtech 9:381-388).

U.S. Pat. No. 4,684,723 discloses a method for separating the alpha-1-proteinase inhibitor from other proteins and nucleic acids present in the plasma or culture medium using ATPS. Also, there is a patent application WO 2010/062244A1, which proposes the recovery and partial purification of therapeutic proteins, particularly monoclonal antibodies, in two stages of extraction in ATPS. In the first stage, the antibodies are partitioned towards the top phase, and in the second phase they precipitate in said phase. They are then recovered and re-dissolved, for further purification by chromatography. In another invention (U.S. Application No. 2010/0179252) the use of a multiphase system is proposed, comprising two types of polymers, one acidic and one etheric, and at least one salt for the separation of biomolecules, cells or particles. Additionally, patent application WO 2010/080062 presents a method for isolating biomolecules in ATPS polymer-salt, wherein the molecule of interest, for example a monoclonal antibody, is partitioned towards the phase that is not rich in the polymer. Additionally, there are studies on the conditions of partition, extraction and purification of antibodies in ATPS (see Andrews, B A, Nielsen, S., Asenjo, J A 2007, "Partinioning and purification of monoclonal antibodies in Aqueous two-phase systems", Bioseparation 6 (5): 303-313; Azevedo, A., Rosa, P., Ferreira, F. Aires-Barros, M. 2007, "Optimisation of Aqueous two-phase extraction of human antibodies", J. Biotechnology 132 (2): 209-217, and Rosa, P., Azevedo, A Sommerfeld, S., Mutter, M Aires-Barros, M., Bäcker, W. 2009, "Application of Aqueous two-phase systems to antibody purification: A multi-phase approach", J. Biotechnology 139(4):306-313).

Moreover, studies have been published on the partition of albumin in this type of systems with respect to variables such as pH, temperature, and type and concentration of polymer and salt. (see Gündüz, U. 2000. "Partitioning of bovine serum albumin in an Aqueous two-phase system: optimization of partition coefficient". Journal of Chromatography B: Biomedical Sciences and Applications, 743 (1-2): 259-262.; Farruggia, B., Nerli, B., Stang, G. 2003. "Study of the serum albumin-polyethyleneglycol interaction to predict the protein partitioning in Aqueous two-phase systems." Journal of Chromatography B. 798 (1): 25-33, Lu, Y., Yang, Y., Zhao, X., Xia, C. 2010 "Bovine serum albumin partitioning in polyethylene glycol (PEG) potassium citrate Aqueous two-phase systems." Food and Bioproducts Processing. 88 (1): 40-46: Garza, M., Rito, M., Serna S., Benavides, J. 2010. "Potential of Aqueous Two-Phase Systems constructed on Flexible devices: Human serum albumin as proof of concept". Process Biochemistry 45 (7)1082-1087).

3. Immunoglobulin Purification Through Precipitation with Caprylic Acid

The immunoglobulin purification technique by caprylic acid precipitation was first introduced by Steinbuch, M., Audran, R., 1969. "The isolation of IgG from mammalian be With The aid of caprylic acid", Arch Biochem. Biophysics 134, 279-284. Subsequently, there were several methodologies based on this principle. For example, U.S. Pat. No. 4,164,495 (Hansen, 1979) uses protein precipitation with 1-8% v/v PEG and 0.1-5% v/v caprylic acid. In U.S. Pat. No. 5,075,425 (Kotitschke et al. 1991) contaminating proteins are precipitated with 2.5% caprylic acid, followed by adsorption on DEAE-Sephadex. Similarly, patent application WO2006064373 (Bloy et al., 2006) proposes the use of 2.5% caprylic acid to precipitate protein contaminants. Also, the U.S. Pat. No. 6,955,917 (Alred et al., 2003) proposes the use of a solution of 40% caprylate (15-50 mM, preferably 20 mM) for removing contaminating proteins and viral inactivation of the product, followed by a on exchange chromatography. This process is similar to that presented by the patent application WO200508293 (Römisch, et al, 2005), in which a solution of caprylate or heptoanate is applied for the same purpose.

Finally, there are patents that propose the use of caprylic acid for other purposes. U.S. Pat. No. 5,164,487 (Kobe et al, 1992) in which caprylic acid at a concentration between 0.4 and 1.5%, is used to remove vasoactive substances and proteolytic enzymes, followed by ion exchange chromatography; and U.S. Patent 20070244305 (Parkinnen, 2007) presents contaminant protein precipitation with PEG, and caprylic acid is used as a step for the inactivation of viruses.

Most methods proposed in these patents have yields around 60%, starting from an initial stage of cold alcohol fractionation.

4. Purification of Albumin

In the case of albumin, the differential thermal denaturation or selective thermo coagulation is a method used for its purification from plasma or a mixture of proteins containing it. U.S. Pat. No. 4,156,681 proposes heating the plasma at 68° C. in ethanol and sodium caprylate, followed, by the addition of PEG to recover the precipitated albumin. Similarly, in U.S. Pat. No. 3,992,367 plasma is heated to 60° C. and then the albumin is precipitated with ethanol. In another invention (U.S. Pat. No. 4,222,934), plasma is heated to 60° C., PEG is added to remove the precipitate of denatured protein, and albumin is recovered by isoelectric precipitation. Moreover, in U.S. Pat. No. 4,177,188 the immunoglobulin is recovered prior to the thermal treatment.

Therefore, there are processes which start from plasma, serum, some fraction of Cohn method or other starting material containing albumin and/or immunoglobulin for recovery thereof, and subsequently employing selective thermo coagulation and the caprylic acid precipitation to purify albumin and immunoglobulin respectively. However, to date the use of such purification techniques from fractions derived from an aqueous two-phase system (ATPS) has not been reported.

The present invention overcomes the limitations of the prior art, since it presents a production line for obtaining injectable formulations of blood-derived protein products with reduced viral load for human use, an utmost important aspect that has not been described in the prior art with respect to obtaining immunoglobulin and albumin using ATPS.

BRIEF SUMMARY OF THE INVENTION

An object of the present invention is a method for the production of injectable formulations of blood-derived protein products with reduced viral load, which method comprises the steps of (FIGS. 1 and 4):
  a. fractionating the starting material in aqueous two-phase system by adding a polymer and at least one salt;
  b. adding phenol to the aqueous two-phase system as a first viral inactivation step;
  c. separating the upper and lower phases of aqueous two-phase system;
  d. purification of the products contained in the upper phase of the system by precipitation with a fatty acid;
  e. purification of the products contained in the lower phase of the system by thermo coagulation;
  f. removing of denatured protein precipitate formed during the purification steps of upper and lower phase of the two-phase system;
  g. increasing the purity of the purified products from the upper and lower phase by chromatography;
  h. nanofiltration of the products obtained in the previous step to remove viral particles;
  i. formulation, stabilization and sterilization of the products obtained.

The method of the invention can be carried out starting from a material that can be selected from a group consisting of blood plasma, blood serum, a fraction obtained by Cohn's method or any other material containing blood-derived protein products, particularly albumin and/or immunoglobulin.

Initially, the fragmentation of the starting material in a system is performed, comprising two aqueous phases. To do so, a polymer and a salt are added, wherein the selected polymer is polyethylene glycol with molecular weight between 1000-6000 Da, and preferably 3350 Da polyethylene glycol, which is used at a concentration in the range between 6 to 15% w/v, preferably between 6 and 9% w/v.

The salt used in the fractionating may be monobasic potassium phosphate, dibasic potassium phosphate, monobasic sodium phosphate, dibasic sodium phosphate, ammonium sulfate and sodium citrate, preferably being used potassium phosphate monobasic and dibasic, at concentrations between 10 and 20 w/v, and preferably between 15 and 20% w/v.

Additionally, a salt which is not involved in the formation of the two phases is employed, but which influences the partitioning of solutes in the system, preferably using sodium chloride at a concentration between 5 and 20 w/v, preferably between 12 and 15% w/v.

This fractionation step is performed at a pH between 5.5 and 7.5, and preferably at a pH of about 6, and is performed at room temperature (20-25° C.).

As a first viral inactivation step, the method of the invention employs phenol between 0.05 and 0.3% v/v, in a preferred embodiment uses phenol at 0.25% v/v.

After viral inactivation, we proceed to the separation of the upper and lower phases of the aqueous two-phase system using a combination of processes that can be selected from: rest and separation, rest and filtration, rest and decantation or simply centrifugation.

The next step is the purification of the products contained in the upper phase of the ATPS obtained. This phase is rich in immunoglobulin, and fir its purification a caprylic acid precipitation is carried out, the latter at a concentration between 1 and 6% v/v, preferably at a concentration between 1.5 and 2% v/v.

Thermo coagulation is also performed for the purification of the products that are in the bottom phase of the system, which is rich in albumin. This process is carried, out at a temperature between 60 and 70° C., preferably at 65° C. This operation is carried out in the presence of sodium caprylate at 0.012 M and 9% ethanol v/v.

To increase the purity of the products obtained in the upper phase of the system, a chromatographic step is employed comprising ion exchange chromatography, affinity chromatography or hydrophobic exchange chromatography. The final purification stage of the products obtained in the lower phase of the system is carried out using ion exchange chromatography.

The removal of viral particles from the products obtained as a result of the process of the present invention is carried out by nanofiltration, employing a 20 nm excluding filter. The products can be stabilized with agents such as sucrose and sodium caprylate to a solution of immunoglobulin and albumin, respectively. The immunoglobulin formulation can be maintained in solution or lyophilized. In the case of albumin a final step of pasteurization for 10 hours at 60° C. is included. Finally, the obtained products are sterilized through a 0.22 mm exclusion membrane.

Other objects of the present invention are the products obtained by the previously described method. The albumin as well as the immunoglobulin obtained through the preferred embodiments of the invention are injectable quality solution products, having a reduced viral load in accordance with the established specifications (WHO, 2010. Guidelines for the Production, Control and Regulation of Snake Antivenom Immunoglobulins, WHO, 2004. Guidelines on viral inactivation and removal Routines Intended to ECOG the viral safety of human blood plasma products).

DETAILED DESCRIPTION OF THE INVENTION

This invention consists of a method for the purification of plasma (blood) derived protein products and is particularly useful in the simultaneous recovery of injectable quality immunoglobulin and albumin from mixtures that may contain these, and other, proteins. This method is practical and economical because it uses affordable reagents and, unlike the Cohn method, does not need specific equipment to meet strict temperature requirements. The products obtained using this method, (mainly immunoglobulins and albumin) present high levels of quality (>90%) and performance. The method can be used in the recovery of other blood proteins, other than immunoglobulin and albumin, such as coagulation factors. It can also be used for the purification of immunoglobulin fragments (F(ab')2 or Fab) obtained through the enzymatic digestion of plasma or from the purified immunoglobulins. Moreover, the process for obtaining each product includes 2 inactivation and 1 viral removal steps, which lead to a reduction in the viral load that ensures its safety, as established in the regulations. Furthermore, this methodology can be used for antibody purification from hyper immune plasma, for example, for the production of anti-venoms and antitoxins.

The starting material may be plasma or serum, digested or not, with proteolytic enzymes, some fraction from the plasma or serum, or any mixture containing immunoglobulin and/or albumin of human origin, or from any other animal.

Figure 1:
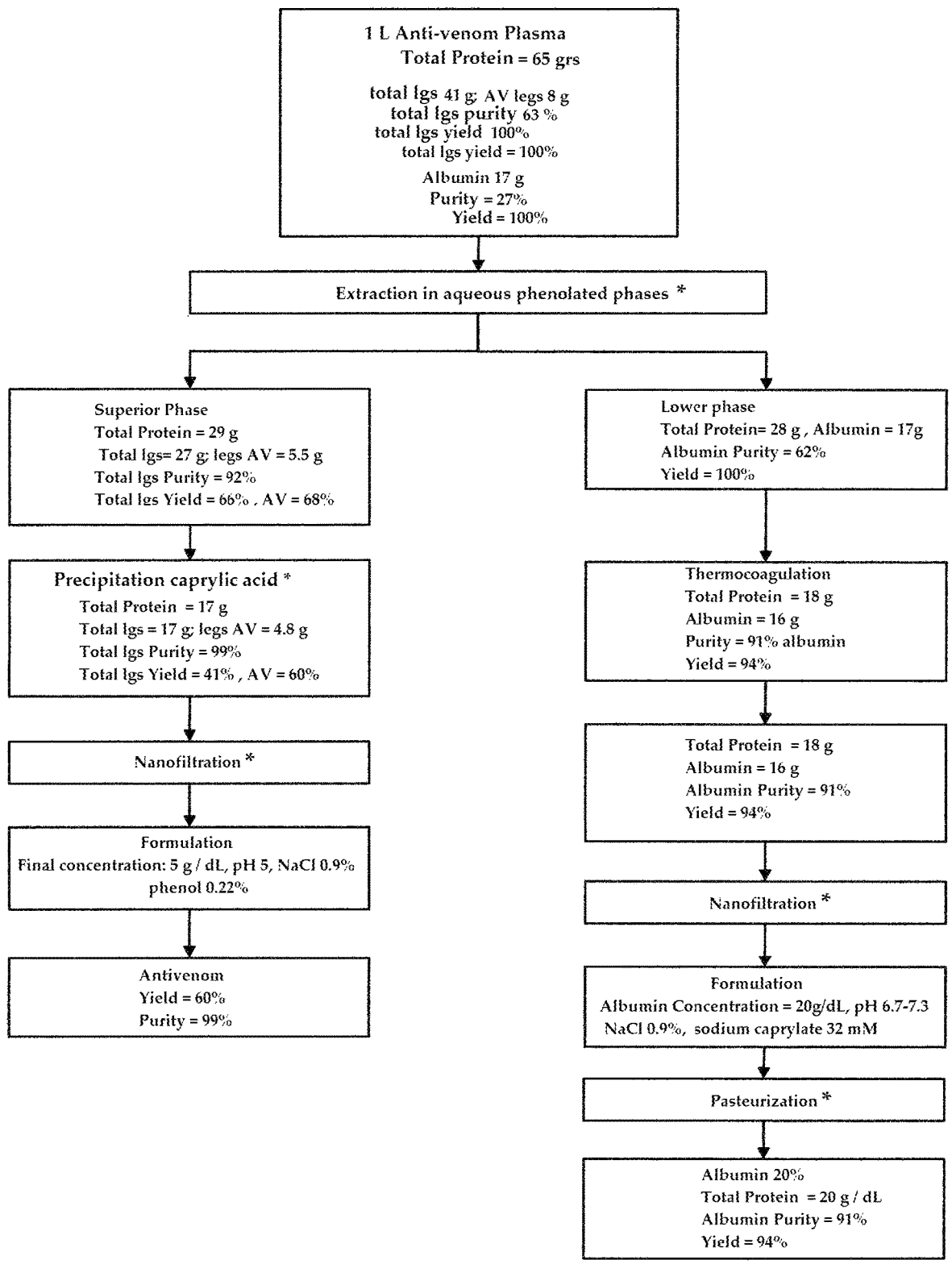
FIG. 1. Flowchart representing the method of the invention for obtaining protein products derived from virus-free hyper immune equine plasma. It shows the value of yield and purity of the products obtained at each stage of the process. Operations with asterisk show viral inactivation or removal steps. Key: Igs=immunoglobulin, AV=antivenom.
Figure 4:
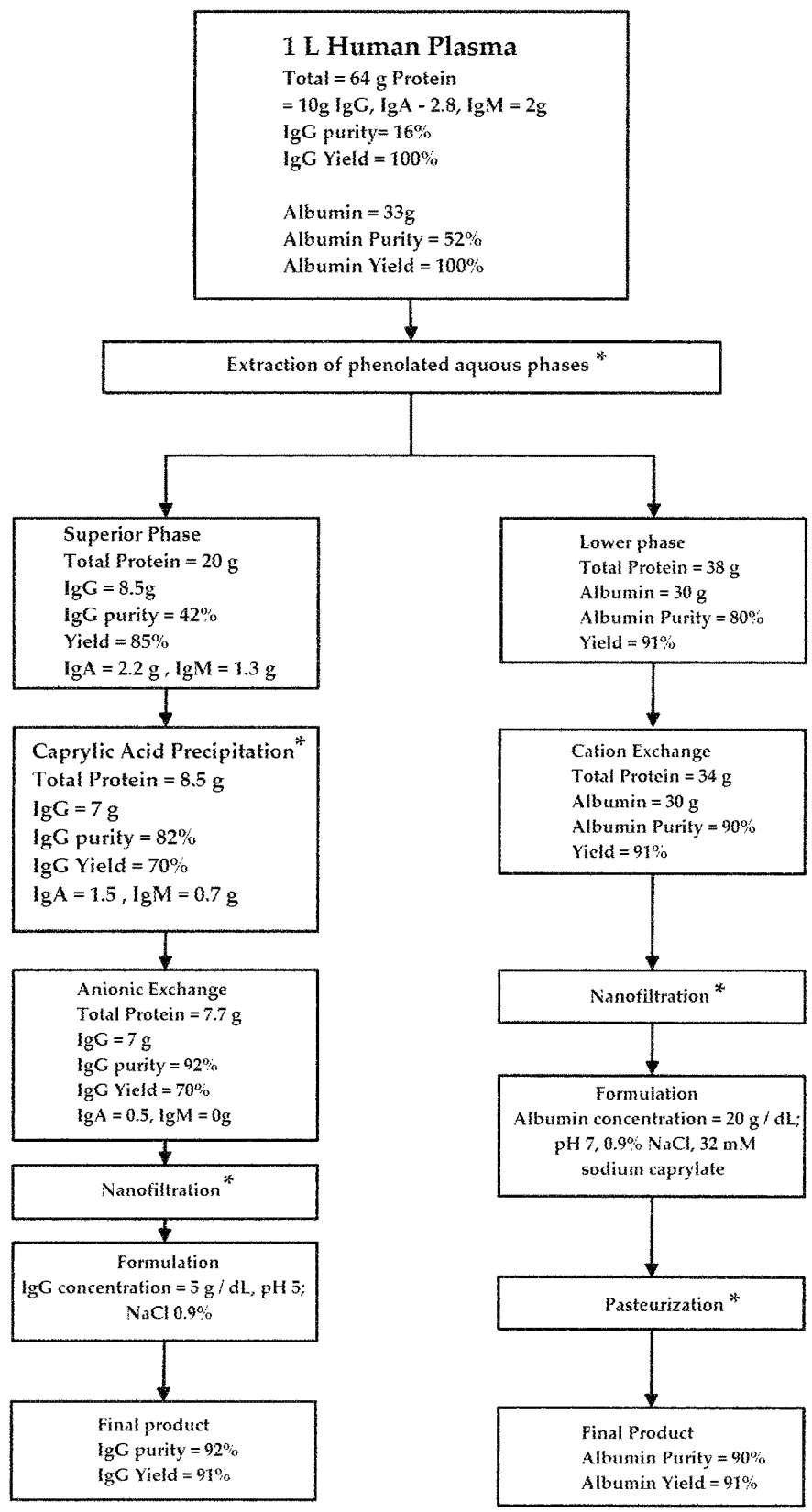
FIG. 4. Flowchart representing the method of the invention for obtaining virus-free protein products derived, from human plasma for intravenous use. It shows the yield and purity of the products obtained at each stage of the process. Operations with asterisk show viral inactivation or removal steps. Key: Igs=Immunoglobulin.

The starting material fractionation is carried out through ATPS (FIGS. 1 and 4). In this kind of separation, the product in interest has an affinity towards one of the two aqueous phases that make up the system, different from the rest of the components of the mixture in which it is found. The phases are formed by mixing two or more hydrophilic substances that, in certain concentrations, become immiscible in water, based on the thermodynamic forces related to their hydration. The water in the system is the water present in the starting material. The system includes the use of a water soluble polymer, a water soluble salt and a water soluble salt that is involved in the fractionation of the solutes but that is not part of the formation of the two phases. The polymer is polyethylene glycol (PEG) with a molecular weight range of 1000 to 6000 Da, which is mostly separated in the upper phase; the salt is potassium phosphate, di and monobasic, which is mostly separated in the lower phase, and the salt that is not involved in the formation of the phases is sodium chloride. The ratio between the monobasic and dibasic potassium phosphate determines the system pH; as the monobasic potassium phosphate increases, the pH decreases. The desired fractionation of proteins takes place in a pH range of 5.5 to 7.5, at room temperature (20-25° C.). Furthermore, the addition of phenol is done to inactivate viral particles that are present in the starting material during fractionation. The antiviral capacity of phenol lies in its ability to produce a physical disruption of the protein and lipid structures of the virus.

The system components are added to the starting material, while stirring constantly (under constant stirring), in the following concentrations: phenol between 0.05-0.3% w/v, PEG between 6-15 w/v %, potassium phosphate between 10-20 w/v % and sodium chloride between 5-20% w/v; more preferably, at 0.25% v/v of phenol, between 6 and 9% w/v of PEG, between 15 and 20% w/v of potassium phosphate and 15% w/v of NaCl. The order in which the components are added may vary, however, it is recommended that each component is added after the previous one has been completely dissolved. Once the components have been added, the mixture is stirred for one additional hour. After this, the mixture is left to rest, so that the phases may form. (It should be noticed) Note that the component concentrations are expressed as w/v (weight/volume) because the starting material provides the water that makes up the ATPS, therefore, the components are advantageously added in their solid forms and not as solutions. This is an improvement when scaling the method since it does not need to prepare multiple component solutions and handle various containers therewith.

Once the phases are formed, different environmental characteristics and the characteristics of the protein themselves, such as the proteins molecular weight, protein concentration, pH, ionic strength and the concentration of the system components, determine their fractionation. Under these conditions, albumin and other contaminant proteins are partitioned towards the lower phase that is rich in salts, and the immunoglobulins and other contaminant proteins are partitioned towards the upper phase. The immunoglobulins, unlike the albumin that remains in suspension, precipitate in the upper phase, which allows their concentration in this phase in just one step. This is another improvement, since the method combines two unit operations such as the primary purification and the concentration of these proteins.

Phase separation is carried out by filtration, centrifugation or decanting. From this point, each phase becomes a parallel line of purification. Both lines will be disclosed separately as follows (FIGS. 1 and 4):

Immunoglobulin Purification from the Upper ATPS Phase.

The precipitate recovered from the upper phase, once the phases have been separated, is suspended again in a volume of water that allows the complete precipitate dissolution; preferably a volume that is less than or equivalent to the initial volume, in order to bring about the right concentration of the product. The suspension is stirred until the paste is completely dissolved. Then, a fatty acid is added, which precipitates and denatures the contaminant proteins, leaving the immunoglobulins in suspension. The fatty acid works within a 1-6% v/v range, preferably between 1.5 and 2 v/v. The fatty acid may have 6 to 8 carbons, preferably 8 carbons (caprylic or octanoic acid). Precipitation can be carried out in a 5 to 8 pH range without affecting the results obtained. The stirring during precipitation must be vigorous and carried out over a 30 to 60 minutes. Then, the precipitate is removed through microfiltration or centrifugation. In addition, this step works as an inactivation step for lipid enveloped viruses. The non-ionized form of the caprylic acid is lipophilic and has the ability to break and penetrate the lipid bilayer of the virus and the proteins associated to it.

Later, the filtrate or supernatant, in which the immunoglobulins are present, is passed through a chromatographic column, which may be selected from the anion-exchange, affinity and hydrophobic exchange groups of chromatography, in order to increase its purity.

Albumin Purification from the Lower ATPS Phase.

The albumin enriched lower phase (FIGS. 1 and 41) is dialyzed or diafiltrated in order to remove the salts from the ATPS. This process is carried, out with a molecular sized membrane, smaller than or equivalent to 30 kDa. Then, the solution is submitted to a selective thermo coagulation process, in which it is heated within a temperature range from 60-70° C. preferably 65° C., for 0.5 to 2 hours. This step precipitates the remaining proteins and leaves the albumin in the solution, since the other plasma proteins are denatured at this temperature. Agents such as sodium caprylate and sodium N-acetyltryptophonate are used to maintain the albumin stability at these temperatures, preferably sodium caprylate at a range of 0.02 to 0.1 M, and more preferably at 0.012 M. This heating is conducted in the presence of 5-15% v/v of ethanol, more preferably at 9% v/v, in order to foster the precipitation of the remaining proteins. After the solution is heated, it is brought back down to room temperature and the pH is adjusted to 5. The precipitate is then separated through microfiltration or centrifugation and the albumin in suspension is recovered. As a final step in the purification of the product, the solution is passed through a chromatographic column, with a particular procedure, through a cationic exchange resin (sulfonic acid or carboxymethyl).

Nano Filtration, Formulation, Stabilization and Packaging of the Two Pharmaceutical Formulations Both solutions of albumin and immunoglobulins are nano filtered, formulated, stabilized and packaged in a similar manner (FIGS. 1 and 4). Nano filtration is a viral removal step based on exclusion through size and uses a 20 μm filter. Viral particles can be removed as antibody-virus complexes due to the presence of antiviral antibodies in the immunoglobulin solutions, or as viral particles, in the case of the albumin formulation. After each solution has been nano filtered, the corresponding medications are formulated. The immunoglobulins formulation includes: the product concentrated from 1.0 to 10.0 g/dL of protein through ultrafiltration with a 30 kDa exclusion membrane; at a pH in a range between 5 and 7, preferably 5; 5% sucrose as a stabilizer and 0.9% NaCl. The product is sterilized through filtration with a 0.22 μm exclusion membrane and then it is packaged. The product may be freeze-dried or may remain in its liquid form.

For albumin, after nano filtration, the formulation involves: the product concentrated at 20 g/dL of protein through ultrafiltration with a 10 kDa exclusion membrane; at a in a range between 6.5 and 7.5, preferably 7; sodium caprylate (%????) as a stabilizer and 0.9% NaCl. The medication is sterilized, packaged and then pasteurized at 60° C. for 10 hours. Pasteurization inactivates enveloped and non-enveloped viruses through the exposure to high temperatures. According to Kempf, C., Stucki, M., Boschetti, N. 2007. "Pathogen inactivation and removal procedures used in the production of intravenous immunoglobulins", Biologicals 35: 35-42, pasteurization acts on the lipid bilayer of the enveloped viruses and stabilizes the virion by transforming the lipids from a solid to a liquid state.

The method of the invention may be better understood with the following working examples, which are provided solely for illustrative purposes of this invention and should in no way be considered as a restriction of its scope.

EXAMPLES

Figure 2:
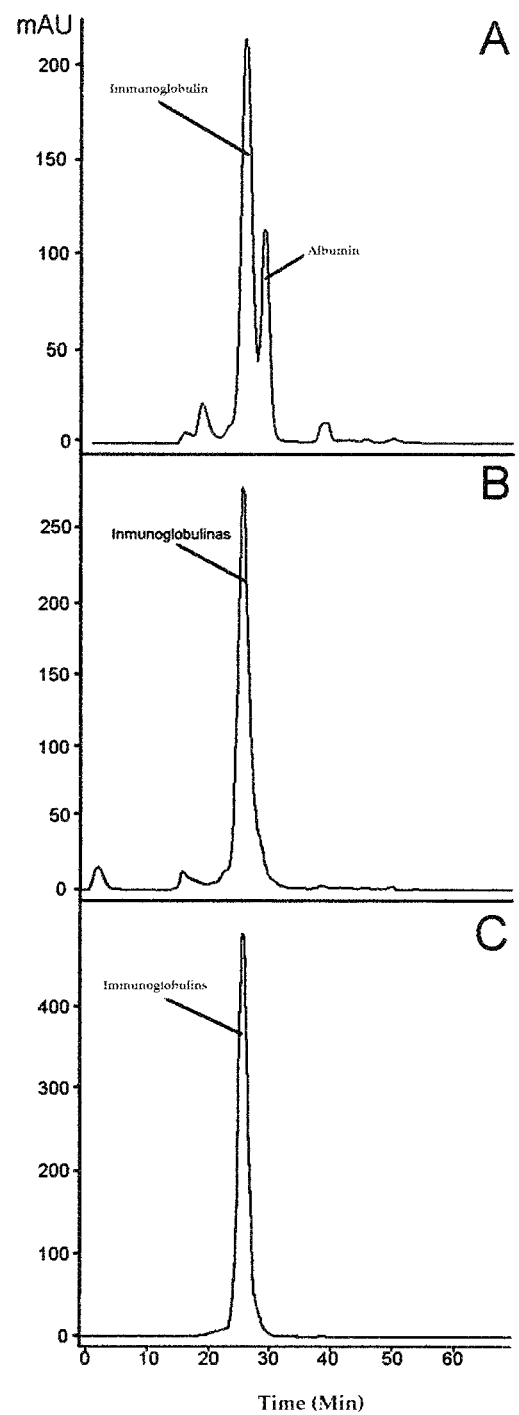
FIG. 2. Gel filtration of samples of the proposed method for producing antivenom from hyperimmune equine plasma. Superdex 200 10/300 GL, column was used, the elution was performed with a 150 mM NaCl buffer. 20 mM Tris-HCl, pH 7.5. A. hyperimmune equine plasma B. Resuspended ATPS top phase. C. Filtrate obtained from caprylic acid precipitation.

Example 1. Production of Anti-Venoms and Albumin from Hyper Immune Equine Plasma In order to obtain immunoglobulins and albumin from the same batch of plasma, 1 L of hyper immune equine plasma, i.e. plasma that is rich in snake anti-venom antibodies, was fractionated in an aqueous two phase polymer salt system. The plasma was obtained from horses that were immunized with venom from *Bothrops asper, Lachesis stenophrys* and *Crotalus simus*. The starting material contained 63% immunoglobulins and 27% albumin (FIGS. 1 and 2). To form the two phase system, 150 g of sodium chloride (15% w/v), 106 g of dibasic potassium phosphate, 74 g of monobasic potassium phosphate (18% w/v), 90 g of polyethylene glycol (9% w/v) and, as an antiviral, 2.5 mL of phenol (0.25% v/v) were added. A ratio of 0.7 was used for dibasic/monobasic potassium phosphate so that the system pH would be 6.1. The mixture was stirred after the addition of each component in order to dissolve it completely before adding the next one. The system was stirred vigorously for 1 additional hour and then was left to rest for one hour to form the phases; an upper phase towards which the immunoglobulins-precipitate and a lower phase which contains the albumin in suspension. Then, the mixture is micro filtered by gravity. This step can also be accomplished by centrifuging or decanting. After (immunoglobulins) the filtrate (albumin) continue being separately processed. As shown in FIG. 1, once the phases have been separated, 68% of the immunoglobulins in the plasma were recovered the upper phase (FIG. 2B), and 100% of the albumin in the plasma was recovered from the lower phase (FIG. 3B). The purity value for each of these products was estimated through gel filtration and corresponds to purities of 92 and 62%, respectively. The overall protein yield between the two phases was of 88%, with the other 12% being fibrin, which is partitioned towards the upper phase (FIG. 1).

To prepare the anti-venom, the precipitate is suspended again in 1400 mL of deionized water and stirred constantly for one hour. Once the immunoglobulins and the other remaining proteins are dissolved, caprylic acid is added. Normally, the amount of caprylic acid that is used in the production of anti-venom is 5-7% v/v. However, in this case, since the fraction of immunoglobulin is derived from the ATPS, it contains fewer contaminants, therefore less caprylic acid is needed (1.75% v/v). After the caprylic acid is added, the mixture is stirred vigorously for 30 minutes in order to foster precipitation. This step has a dual purpose; on the one hand, it precipitates the contaminant proteins and, on the other hand, it inactivates the enveloped viruses. Then, the immunoglobulins in the solution are recovered through microfiltration by gravity. At this point, 60% of the anti-venom immunoglobulins that were originally present in the plasma is recovered with a purity of 99% (FIGS. 1 and 2). Since the product had a very high level of purity, an additional chromatographic step was not necessary and the product was directly formulated.

The filtrate was then dialyzed against deionized water with a 15 kDa exclusion membrane. Dialysis may be replaced by diafiltration through ultrafiltration. As a third antiviral step, the anti-venom is nano-filtered through a 20 µm exclusion filter. The product was then concentrated through ultrafiltration with a 30 kDa exclusion membrane to the protein concentration required to achieve the specifications for a neutralizing activity (for example, 3 tug venom/mL anti-venom for Bothrops asper, 3 mg venom/mL anti-venom for Lachesis stenophrys, 2 mg, venom/mL antivenom for *Crotalus simus* or 0.5 mg venom/mL anti-venom for *Micrurus nigrocinctus*). The product was formulated at pH 7 with 0.9% NaCl w/v and 0.25% phenol w/v, and sterilized through filtration with a 0.22 µm exclusion membrane (FIG. 1). The product was then dispensed in sterile flasks, 10 mL in each one.

In addition to this, the lower ATPS phase, which is rich in albumin, was dialyzed against water with a 15 kDa exclusion membrane in order to remove the salts resulting from the system. The dialysis can be replaced with diafiltration through ultrafiltration. To precipitate the contaminant proteins, the albumin suspension is submitted to thermo coagulation, for which 2.4 g (0.012 M) of sodium caprylate as a stabilizer and 126 mL of 95% ethanol v/v (9% v/v) was added. The mixture was then heated for one hour at 65° C. in a temperature controlled water bath. It was then cooled to room temperature and the pH was adjusted to 5 with HCl 0.5 M. The protein precipitates were removed through microfiltration by gravity. As shown in FIGS. 1 and 3C, this step provided a yield of 94% with a purity of 91%.

To refine the purity of the purified albumin rich filtrate, 0.1% NaCl was added and the pH was adjusted to 8 with NaOH 0.5 M. It was then passed through a cationic exchange membrane with a sulfonic acid resin. The free fraction was recovered, and the pH was adjusted to 7 with HCl 0.5 M. As a second antiviral step, the solution was then nano filtered through a 20 µm exclusion membrane. The product was concentrated through ultrafiltration with a 10 kDa exclusion membrane to 20 sodium caprylate was added as a stabilizer and the pH was adjusted to 7. The product was sterilized through filtration with a 0.22 µm exclusion membrane and dispensed into sterile bottles. The product was then pasteurized for 10 hours at 60° C. to guarantee its viral safety (FIG. 1).

Figure 5:
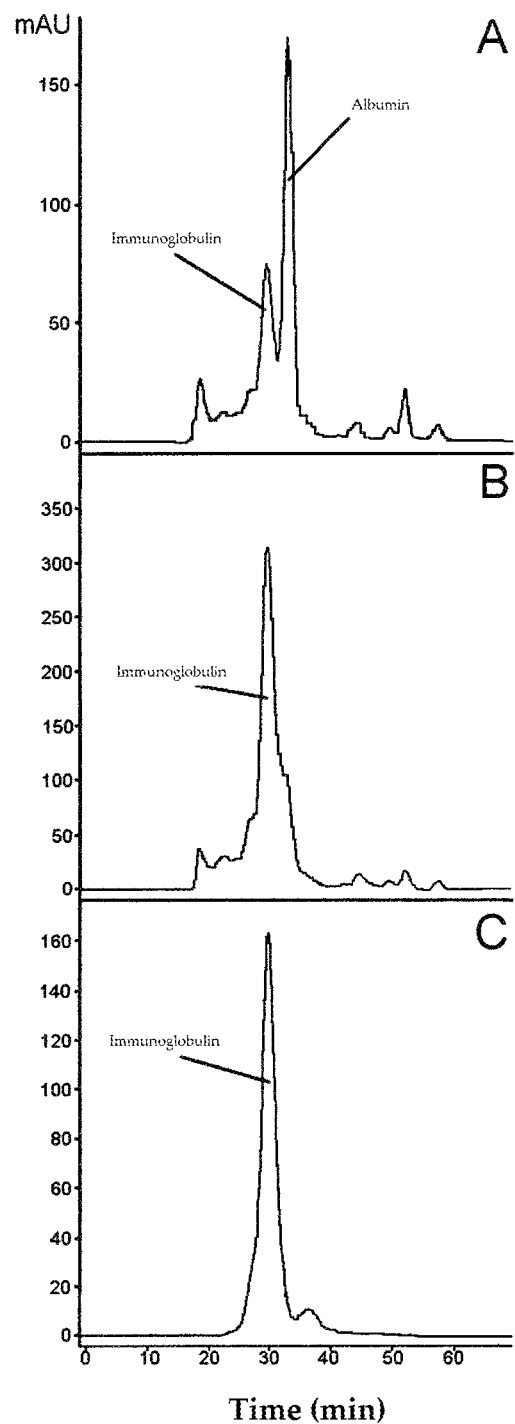
FIG. 5. Gel filtration of samples of the proposed method for obtaining, gammaglobulin from human plasma. Superdex 200 10/300 GL column was used, elution was performed with a 150 mM NaCl buffer, 20 mM Tris-HCl, pH 7.5. A. Human plasma. B. Resuspended ATPS top phase. C. Anion exchange chromatography of the filtrate obtained after caprylic acid precipitation.
Figure 6:
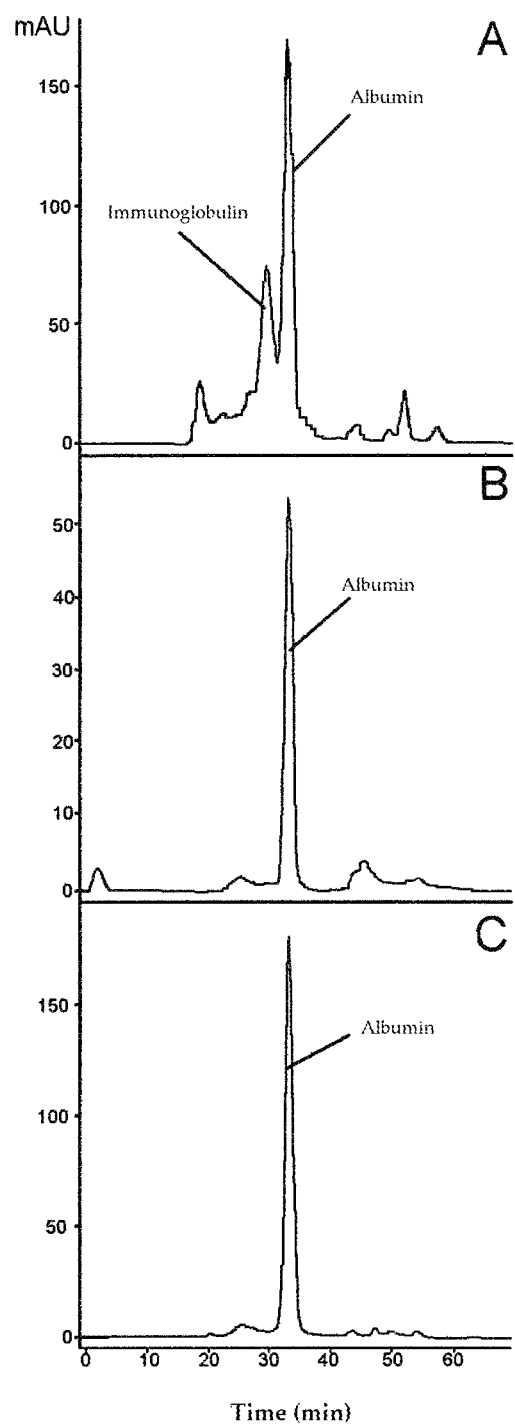
FIG. 6. Gel filtration of samples of the proposed method for obtaining human albumin. Superdex 200 10/300 GL column was used, elution was performed with a 150 mM NaCl buffer, 20 mM Tris-HCl, pH 7.5. A. Human plasma. B. ATPS lower phase. C. Cation exchange chromatography of lower phase.

Example 2. Production of Virus Free Injectable Quality Immunoglobulins and Albumin from Human Plasma One liter of human plasma was fractionated in an aqueous polymer salt ATPS in order to obtain immunoglobulins and albumin, it should be noticed that human plasma contains a higher proportion of albumin (52%) compared to immunoglobulins 16%). To form the two phase system, 150 g of sodium chloride (15% w/v), 106 g of dibasic potassium phosphate, 74 g of monobasic potassium phosphate (18% w/v), 60 g polyethylene glycol (6% w/v) and, as an antiviral agent, 2.5 of phenol (0.25% v/v) were added. In this case, a lower concentration of PEG was used in comparison with the Example 1 because the starting material, in this case human plasma, has a lower percentage of immunoglobulins, thus it requires less of the upper phase in which these proteins are partitioned. All other operations in the step of fractionation were carried out in the same manner as in Example 1. As shown in FIGS. 4 and 5B, the recovery of immunoglobulins in the upper phase was 85% with a purity of 42%, while the protein yield for albumin in the lower phase was of 91% with a purity of 80% (FIGS. 4 and 6B). The overall protein yield for the system was 91% and the remaining percentage corresponds to fibrin.

Once the two phases were separated, the upper phase that is rich in precipitated immunoglobulins, was suspended again in 1400 mL of deionized water and stirred constantly for 1 hour. Once the immunoglobulins and other remaining proteins were dissolved, caprylic acid at 2% V/V was added. The filtrate recovered presented an immunoglobulin yield of 70%, with a purity of 82% (FIG. 4).

Unlike Example 1, once the filtrate from the precipitation with caprylic acid was recovered, an anionic exchange chromatography was carried out in order to refine the purity of the immunoglobulin solution (FIG. 4). For this, 0.1% NaCl was added, the pH was adjusted to 5 with HCl 0.5 M, and the mixture was passed through an anionic exchange membrane with a quaternary ammonium resin. The free fraction was recovered and the pH was adjusted to 7 with NaOH 0.5 M. In this fraction, 70% of the immunoglobulins originally present in the starting material were recovered, with a purity of 92%, which was determined through gel filtration (FIGS. 4 and 5C). It should be noticed that precipitation with caprylic acid and chromatography are effective processes in removing IgA and IgM. The product obtained was formulated, stabilized and sterilized as described in Example 1 for the anti-venom solution.

With regard to the lower ATPS phase that is rich in albumin, it shown a purity of 80%, with a recovery yield of 91% (FIG. 6B), and for this reason, after dialysis, selective thermo coagulation of the solution was not carried out. Therefore, the purity of the albumin was increased through cationic exchange chromatography, which was conducted under the same conditions described above in Example 1 for equine albumin. Moreover, the remaining operations were also carried out in the same manner as described above for equine albumin. Ultimately, a product with a purity of 90% and a recovery yield of 91% was obtained (FIGS. 4 and 6C).

Example 3. Determination of Anti-Venom Immunoglobulin Purity and Yield

Figure 3:
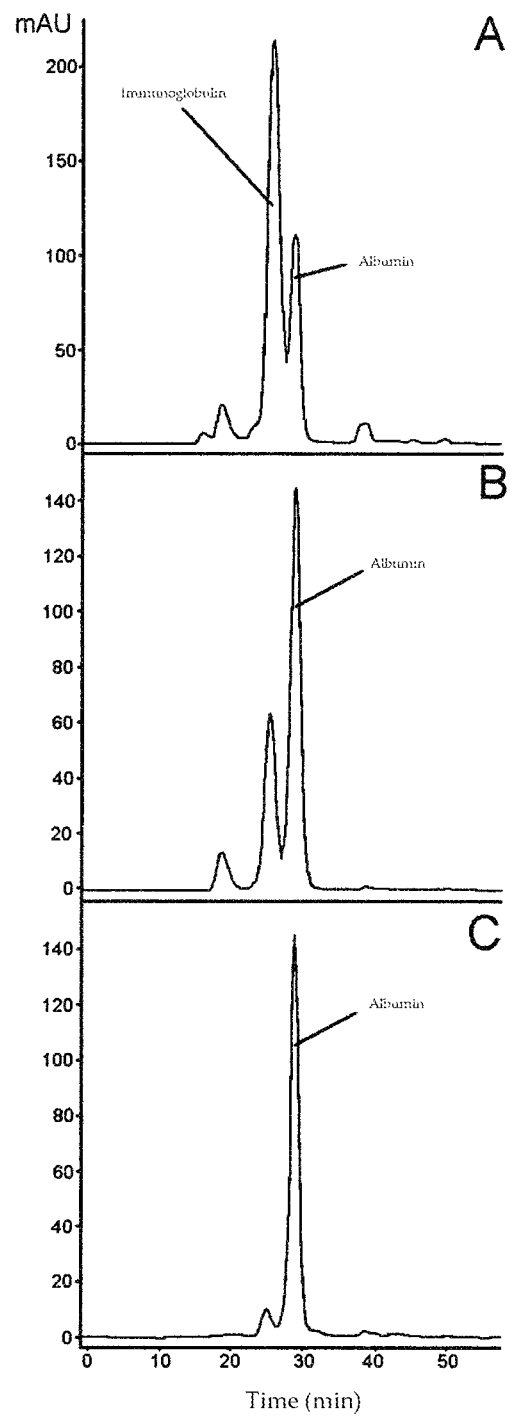
FIG. 3. Gel filtration of samples of the proposed method for obtaining equine albumin. Superdex 200 10/300 GL column was used, elution was performed with a 150 mM NaCl buffer, 20 mM Tris-HCl pH 7.5. A. hyperimmune equine plasma. B. ATPS lower phase. C. Cation exchange chromatography of the filtrate obtained after thermo coagulation.

The purity analysis of the starting material and the samples taken from each step in the purification process was carried, out with gel filtration in FPLC (FIGS. 2 and 3). A Superdex 200 10/300 GL column was used, and elution was performed with NaCl 150 mM, Tris-HCl 20 mM, pH 7.5 buffer. The purity percentage of the total immunoglobulins was calculated as the ratio between the area under the curve of the peak with a retention time of 25±0.3 min (corresponding to the molecular weight of the immunoglobulins), and the total area under the curve of all the chromatogram peaks.

To determine the protein yield, the total protein concentration of the starting material and the samples taken from each step of the purification process was quantified, using a modified Biuret method (see Parvin, R., Pande, S. V. Venkitasubramanian, A. 1965. "On the colorimetric Biuret Method of Protein Determination". Analytical Biochemistry 12: 219-229). With the data obtained from the protein determination, the percentages of purity through FPLC and the volume of each sample, the total amount of immunoglobulins obtained was expressed in grams. Lastly, the protein yield was calculated based on the ratio between total immunoglobulins in the sample (g), and total immunoglobulins in the starting material (g).

Furthermore, an ELISA was carried out on the starting, material and the samples taken from each step of the purification process or the quantification of specific anti-venom antibodies for *Bothrops asper*. For this, 96 wells plates were covered with 100 µL/well with a solution of *B. asper* venom in a phosphate solution (3 µg/well), followed with overnight incubation at room temperature. Then, several dilutions of the samples were added in triplicate at 100 µL/well and incubated for 1 hour at room temperature. After washing the plate, 100 well of a dilution of a conjugated equine anti IgG coupled with peroxidase was added and then incubated for an hour. After washing the plate one more time, the substrate (hydrogen peroxide and o-phenylenediamine) was added in order to develop color. The absorbency was read in a micro plate reader at 492 am. The equine IgG anti-venom was expressed in terms of g/L, using a standard calibration curve prepared with known anti-venom IgG. Said standard was obtained through affinity chromatography, by passing a partially purified hyper immune equine sample through a Sepharose column, coupled with *B. asper* venom.

Based on the concentrations obtained with ELISA from the anti-venom immunoglobulins samples and the volume of each one, the amount of anti-venom immunoglobulins were expressed in grams. Lastly, the protein yield was calculated based on the ratio of anti-venom immunoglobulins in the sample (g) and anti-venom immunoglobulins in the starting material (g).

Example 4. Determination of Human Immunoglobulin Purity and Yield

The determination of the protein yield for the starting material and the samples from each step of the purification process was carried out as in Example 3.

For the quantification of IgG, IgA and IgM, a radial immunodiffusion kit (RID) was used. (Cromatest, Linear Chemicals SL, Barcelona, Spain). Samples were applied in wells with agarose gel and allowed to diffuse for 48 hours. Based on the concentration achieved and the volume for each sample, each type of antibody was expressed in terms of grams. From the above data, the gamma globulin (IgG) purity in each simple was determined, based on the ratio of the immunoglobulins amount obtained through RID and total protein in the sample. Furthermore, the gamma globulin yield was calculated based on the ratio of gamma globulin in the sample (4) and the gamma globulin in the starting material (g).

Example 5. Determination of Albumin Purity and Yield

This determination was carried out similarly to both, equine and human albumin. With regard to the purity of albumin, this was determined by gel filtration on FPLC (FIGS. 3 and 6), as described for immunoglobulins. Purity was defined based on the ratio between the area under the curve of the peak with a retention time of 28±0.3 mm (corresponding to the molecular weight of albumin), and the total area under the curve of all the peaks in the chromatogram.

The protein yield was determined as specified for immunoglobulins, it means, based on the ratio of albumin in the sample (g) and albumin in the starting material (g).

The invention claimed is:

1. A method for the simultaneous recovery of immunoglobulins and albumin from a starting material selected from the group consisting of blood, plasma, serum, a fraction obtained through Cohn method and materials containing plasma derived protein products, for the production of injectable formulations with reduced viral load, said method comprising:

adding a polymer, at least one salt and phenol to the starting material under constant stirring, wherein each one of the polymer and the at least one salt is added in solid form and not as solutions in the starting material, thereby obtaining a mixture;

leaving the mixture from the previous step to rest so that an aqueous two phase system is formed;

separating an upper and a lower phase from the aqueous two phase system formed in the previous step thereby simultaneously recovering immunoglobulins from the upper phase and albumin from the lower phase;

purifying the immunoglobulins in the upper phase through precipitation with a fatty acid;

purifying the albumin in the lower phase through thermo coagulation;

removing denatured protein precipitates formed during the purification steps of the upper and lower phases;

increasing the purity of the immunoglobulins and albumin obtained from the upper and lower phases through chromatography;

nanofiltering the immunoglobulins and albumin obtained in the previous step to remove viral particles; and formulating, stabilizing and sterilizing the simultaneously recovered immunoglobulins and albumin.

2. The method of claim 1, wherein the polymer used in the starting material is polyethylene glycol with a molecular weight ranging between 1000-6000 Da.

3. The method of claim 2, wherein the polymer is polyethylene glycol with a molecular weight of about 3350 Da.

4. The method of claim 3, wherein the polyethylene glycol is in a concentration between 6 and 15% w/v.

5. The method of claim 4, wherein the polyethylene glycol is in a concentration between 6 and 9% w/v.

6. The method of claim 1, wherein the at least one salt is selected from the group consisting of monobasic potassium phosphate, dibasic potassium phosphate, ammonium phosphate and sodium citrate.

7. The method of claim 6, wherein the salt is monobasic and dibasic potassium phosphate.

8. The method of claim 7, wherein monobasic and dibasic potassium phosphates are in a concentration between 10 and 20% w/v.

9. The method of claim 8, wherein monobasic and dibasic potassium phosphates are in a concentration between 15 and 20% w/v.

10. The method of claim 1, wherein one salt that has influence on the partition of solutes but not on the formation of the two phases is added.

11. The method of claim 10, wherein the salt is sodium chloride.

12. The method of claim 11, wherein sodium chloride is in a concentration between 5 and 20% w/v.

13. The method of claim 12, wherein sodium chloride is in a concentration between 12 and 15% w/v.

14. The method of claim 1, wherein the aqueous two phase system is formed at a pH between 5.5 and 7.5.

15. The method of claim 14, wherein the pH is 6.

16. The method of claim 1, wherein viral inactivation takes place using phenol in a concentration between 0.05 and 0.3% v/v.

17. The method of claim 16, wherein the phenol is at a concentration of 0.25% v/v.

18. The method of claim 1, wherein separating of the upper and lower phases of the aqueous two phase system is performed through a combination of processes selected from the group consisting of settling and separation, settling and filtration, settling and decanting or centrifuging.

19. The method of claim 1, wherein purifying the immunoglobulins contained in the upper phase of the aqueous two phase system is through precipitating with octanoic acid.

20. The method of claim 19, wherein the octanoic acid is in a concentration of between 1 and 6% v/v.

21. The method of claim 20, wherein the octanoic acid is in a concentration of between 1.5 and 2% v/v.

22. The method of claim 1, wherein the thermo coagulation takes place at a temperature of between 60° and 70° C.

23. The method of claim 22, wherein the thermo coagulation takes place at 65° C.

24. The method of claim 1, wherein the thermo coagulation of the lower phase takes place in the presence of sodium caprylate and ethanol.

25. The method of claim 24, wherein the sodium caprylate and ethanol is a mixture of the sodium caprylate at 0.012 M and ethanol at 9% v/v.

26. The method of claim 1, wherein the chromatography is selected from the group consisting of ionic exchange chromatography, affinity chromatography and hydrophobic exchange chromatography.

27. The method of claim 1, wherein the chromatography is ionic exchange chromatography.

28. The method of claim 1 wherein the sterilizing is carried out through a 22 µm exclusion filter.

* * * * *